(12) United States Patent
Mahaney

(10) Patent No.: US 6,388,071 B2
(45) Date of Patent: May 14, 2002

(54) ALKYNYL PHENYL HETEROAROMATIC GLUCOKINASE ACTIVATORS

(75) Inventor: Paige Erin Mahaney, Montclair, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/841,983

(22) Filed: Apr. 25, 2001

Related U.S. Application Data

(60) Provisional application No. 60/201,546, filed on May 3, 2000.

(51) Int. Cl.⁷ .................... C07D 277/46; C07D 413/12
(52) U.S. Cl. .................... 544/133; 544/333; 546/270.7; 548/195; 514/866
(58) Field of Search .......................... 544/133; 548/195

(56) References Cited

U.S. PATENT DOCUMENTS 6,197,970 B1 * 3/2001 Nagasawa et al. .......... 548/195

* cited by examiner

Primary Examiner—Robert W. Ramsuer
(74) Attorney, Agent, or Firm—George W. Johnston; Dennis P. Tramaloni; F. Aaron Dubberley

(57) ABSTRACT

Para-alkynyl phenyl heteroaromatic amides which are active as glucokinase activators to increase insulin secretion which makes them useful for treating type II diabetes.

25 Claims, No Drawings

ALKYNYL PHENYL HETEROAROMATIC GLUCOKINASE ACTIVATORS

PRIORITY TO PROVISIONAL APPLICATION(S) UNDER 35 U.S.C. §119(e)

This application claims priority under 35 U.S.C. §119(e) of provisional application Ser. No. 60/201,546, filed on May 3, 2000.

BACKGROUND OF THE INVENTION

Glucokinase (GK) is one of four hexokinases found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial ($\approx$10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J.*, 10, 1213–1218, 1996). An increase in glucose exposure is coupled through GK in p-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J .Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides a compound, comprising an amide of the formula:

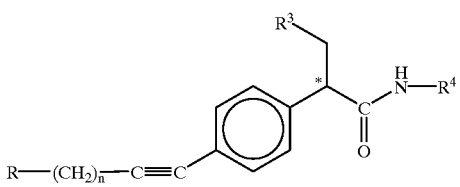

I wherein R is hydrogen, lower alkyl, hydroxy lower alkyl, lower alkoxy lower alkyl,

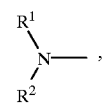

an unsubstituted or hydroxy substituted cycloalkyl ring containing 5 or 6 ring carbon atoms, a five- or six-membered saturated heterocyclic ring, which contains from 1 to 3 hetero ring atoms selected from the group consisting of sulfur, oxygen or nitrogen, or an unsubstituted five- or six-membered heteroaromatic ring, connected by a ring carbon atom, which contains from 1 to 3 heteroatoms in the ring selected from the group consisting of sulfur, nitrogen and oxygen; $R^3$ is cycloalkyl having 3 to 7 carbon atoms; $R^4$ is an unsubstituted or mono-substituted five- or six-membered heteroaromatic ring, connected by a ring carbon atom to the amine group shown, which five- or six-membered heteroaromatic ring contains from 1 to 3 heteroatoms selected from sulfur, oxygen or nitrogen, with one heteroatom being nitrogen adjacent to the connecting ring carbon atom; said mono-substituted heteroaromatic ring being monosubstituted at a position on a ring carbon atom other than adjacent to said connecting carbon atom with a substituent selected from the group consisting of lower alkyl, halo, nitro, cyano, —$(CH_2)_m$—$OR^6$,

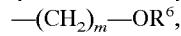

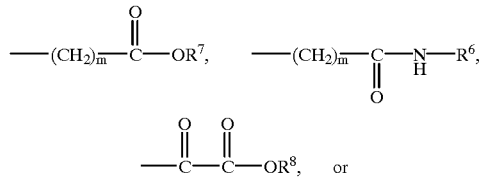

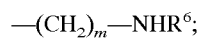

—$(CH_2)_m$—$NHR^6$;

n is an integer from 0 to 2;
m is 0, 1, 2, 3 or 4;
$R^1$, $R^2$, $R^6$, $R^7$ and $R^8$ are independently hydrogen or lower alkyl and * designates the assymetric carbon atom center;
or a pharmaceutically acceptable salt thereof.

The compounds of formula I have been found to activate glucokinase in vitro. Glucokinase activators are useful for increasing insulin secretion in the treatment of type II diabetes in humans.

DETAILED DESCRIPTION OF THE INVENTION

This invention provides a compound, comprising an amide of the formula:

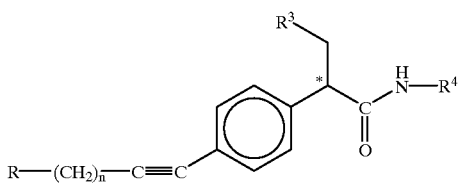

I

In the compound of formula I, the "*" designates the asymmetric carbon atom in this compound with the R optical configuration being preferred. The compound of formula I may be present in the pure R form or as a racemic or other mixtures of compounds of formula I having the R and S optical configuration at the asymmetric carbon shown. The pure R enantiomers are preferred.

As used throughout this application, the term "lower alkyl" includes both straight chain and branched chain alkyl groups having from 1 to 7 carbon atoms, such as methyl, ethyl, propyl, isopropyl, preferably methyl and ethyl. As used herein, the term "halogen or halo" unless otherwise stated, designates all four halogens, i.e. fluorine, chlorine, bromine and iodine.

The term "hydroxy lower alkyl" includes any hydroxy lower alkyl group where lower alkyl is defined as above. The hydroxy can be substituted at any place on the lower alkyl group such as 1-hydroxy ethyl, 2-hydroxy propyl, or 2-hydroxy isopropyl. Lower alkoxy lower alkyl denotes any hydroxy lower alkyl group wherein the hydrogen of the hydroxy moiety is substituted by lower alkyl. The cycloalkyl groups, unless otherwise designated, are those compounds having a ring of from 3 to 7 carbon atoms, particularly cyclopentyl, cyclohexyl, cyclobutyl and cyclopropyl. The preferable cycloalkyl groups contain from 5 to 6 ring carbon atoms.

R can be any five- or six-membered saturated heterocyclic ring containing from 1 to 3, preferably from 1 to 2, heteroatoms selected from the group consisting of sulfur, oxygen or nitrogen. Any such five- or six-membered saturated heterocyclic ring can be used in accordance with this invention. Among the preferred rings are morpholinyl, pyrrolidinyl, piperazinyl, piperidinyl, etc.

As used herein, the term "lower alkanoic acid" denotes lower alkanoic acids containing from 2 to 7 carbon atoms such as propionic acid, acetic acid and the like. The term "lower alkanoyl" denotes monovalent alkanoyl groups having from 2 to 7 carbon atoms such as propionoyl, acetyl and the like. The term "aroic acids" denotes aryl alkanoic acids where aryl is as defined above and alkanoic contains from 1 to 6 carbon atoms. The term "aroyl" denotes aroic acids wherein aryl is any aromatic hydrocarbon containing 6 or 12 carbon atoms, preferably phenyl, and the aroic acids have hydrogen group of the acid COOH moiety removed. Among the preferred aroyl groups is benzoyl.

During the course of the reaction the various functional groups such as the free carboxylic acid or hydroxy groups will be protected via conventional hydrolyzable ester or ether protecting groups. As used herein the term "hydrolyzable ester or ether protecting groups" designates any ester or ether conventionally used for protecting carboxylic acids or alcohols which can be hydrolyzed to yield the respective hydroxyl or carboxyl group. Exemplary ester groups useful for those purposes are those in which the acyl moieties are derived from a lower alkanoic, aryl lower alkanoic, or lower alkane dicarboxylic acid. Among the activated acids which can be utilized to form such groups are acid anhydrides, acid halides, preferably acid chlorides or acid bromides derived from aryl or lower alkanoic acids. Example of anhydrides are anhydrides derived from monocarboxylic acid such as acetic anhydride, benzoic acid anhydride, and lower alkane dicarboxylic acid anhydrides, e.g. succinic anhydride as well as chloro formates e.g. trichloro, ethylchloro formate being preferred. A suitable ether protecting group for alcohols are, for example, the tetrahydropyranyl ethers such as 4-methoxy-5,6-dihydroxy-2H-pyranyl ethers. Others are aroylmethylethers such as benzyl, benzhydryl or trityl ethers or α-lower alkoxy lower alkyl ethers, for example, methoxymethyl or allylic ethers or alkyl silylethers such as trimethylsilylether.

The term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH 2.0 to 3. Particularly preferred amino protecting groups are tertiary lower alkyl, lower alkyl and triloweralkyl methyl ether groups.

The heteroaromatic ring defined by R or $R^4$ can be an unsubstituted or mono-substituted five- or six-membered heteroaromatic ring having from 1 to 3 heteroatoms selected from the group consisting of oxygen, nitrogen or sulfur. The heteroaromatic ring defined by R and $R^4$ are connected to the remainder of the compound of formula I by a ring carbon atom. The heteroaromatic ring which is defined by $R^4$ contains a first nitrogen heteroatom adjacent to the connecting ring carbon atom and if present, the other heteroatoms can be sulfur, oxygen or nitrogen. Such heteroaromatic rings include, for example, pyrazinyl, pyridazinyl, isoxazolyl, isothiazolyl, and pyrazolyl. On the other hand, when R is a heteroaromatic ring, this ring need not contain a nitrogen heteroatom. Among the preferred heteroaromatic rings are included pyridinyl, pyrimidinyl, thiazolyl, and imidazolyl. These heteroaromatic rings which constitute R or $R^4$ are connected via a ring carbon atom to the remainder of formula I. The ring carbon atom of the heteroaromatic ring which is connected via the amide linkage to form the compound of formula I is not substituted with any substituent.

$R^4$ is an unsubstituted or mono-substituted five- or six-membered heteroaromatic ring containing from 1 to 3 hetero atoms selected from the group consisting of nitrogen, oxygen or sulfur with one hetero atom being nitrogen and connected to the remainder of the molecule by a ring carbon atom. In this case, the preferred rings are those which contain a nitrogen heteroatom adjacent to the connecting ring carbon. The preferred five-membered heteroaromatic rings contain 2 or 3 heteroatoms with thiazolyl, imidazolyl, oxazolyl and thiadiazolyl being especially preferred. When the heteroaromatic ring is a six-membered heteroaromatic, the ring is connected by a ring carbon atom to the amine group shown, with one nitrogen heteroatom being adjacent to the connecting ring carbon atom. The preferred six-membered heteroaromatic rings include, for example, pyridinyl, pyrimidinyl, pyrazinyl, pyridazinyl, and triazinyl.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, paratoluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

In accordance with the present invention, preferable residue $R^3$ is cyclopentyl. Preferable residue $R^4$ is thiazolyl, optionally mono-substituted by —$(CH_2)_m$—$C(O)OR^7$, wherein $R^7$ is lower alkyl and m is 0, 1, 2, 3 or 4, preferably 0. Most preferable residue $R^3$ is unsubstituted thiazolyl. Preferable residue R is selected from hydrogen; hydroxy lower alkyl such as hydroxy methyl, 2-hydroxy propyl and 2-hydroxy-2-butyl; lower alkoxy lower alkyl such as methoxymethyl; hydroxy substituted cyclohexyl; morpholino; unsubstituted pyridyl or pyrimidinyl; and —$N(R^1,R^2)$, wherein $R^1$ and $R^2$ each independently denote a lower alkyl residue, preferably methyl, and n in the compound of formula I is 1 or 2, preferably 1.

The preferred compounds of formula I are those compounds where $R^3$ is cyclopentyl (compounds of formula IA). Among the embodiments of compounds of formula IA are those compounds which $R^4$ is an unsubstituted or mono-substituted 5-membered heteroaromatic ring. An embodiment of this invention where $R^4$ is an unsubstituted or mono-substituted 5-membered heteroaromatic ring are those compounds where $R^4$ is an unsubstituted or mono-substituted thiazolyl ring (compound of formula IA-1) with the unsubstituted thiazoles being designated compounds IA-1a and the substituted thiazole being designated IA-1b. Among the embodiments compounds of formulas IA-1a and IA-1b are those compounds where R is hydrogen or lower alkyl, and compounds where R is hydroxy lower alkyl or lower alkoxy lower alkyl Among the embodiments of the compound of formula IA-1b are those compounds where $R^4$ is thiazole mono-substituted with

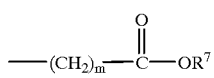

and m and $R^7$ are as above and R is hydroxy lower alkyl.

In accordance with another embodiment of compounds of formulas IA-1a and IA-1b are those compounds where R is

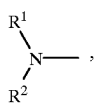

and $R^1$ and $R^2$ are as above (the compound of formula IA-1a(1) and formula IA-1b(2)).

Among the embodiments of the compounds of formula IA-1 a where $R^4$ is an unsubstituted thiazole are those compounds where; i) R is hydroxy substituted or unsubstituted cycloalkyl ring containing from 5 to 6 carbon atoms, a five- or six-membered saturated heterocyclic ring containing from 1 to 2 hetero ring atoms selected from the group consisting of sulfur, oxygen or nitrogen or ii) an unsubstituted five- or six-membered heterocyclic ring containing from 1 to 3 heteroatoms in the ring selected from the group consisting of sulfur, nitrogen or oxygen and n is 0 or 1.

In accordance with this invention, the compounds of formula I are produced by the following reaction scheme:

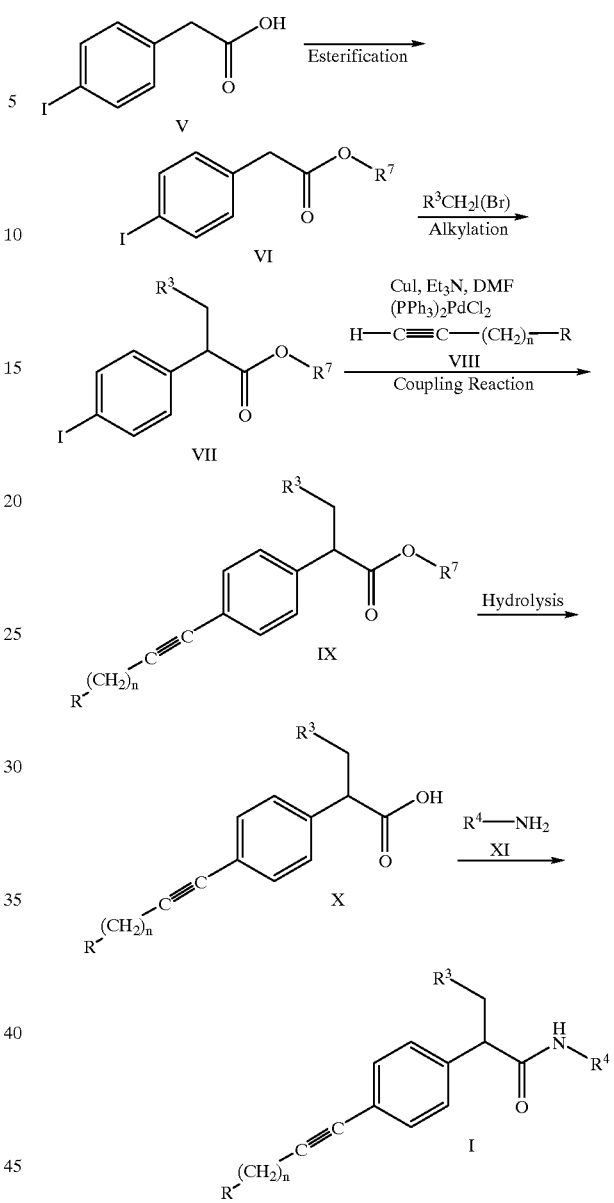

wherein n, R, $R^2$, $R^3$ and $R^4$ are as above, and $R^7$ forms a hydrolyzable ester protecting group.

In accordance with this method, the compound of formula V is converted into the compound of formula VI by protecting the carboxylic acid group in the compound of formula V through the formation of a suitable hydrolyzable ester group. Any conventional hydrolyzable ester protecting group can be utilized in this conversion. In fact, in accordance with the preferred embodiment of this invention, the compound of formula V is reacted with methyl alcohol in the presence of sulfuric acid to form the methyl ester of the compound of formula V which methyl ester is the compound of formula VI. In the next step of the reaction, the compound of formula VI is reacted with the halide shown to form the compound of formula VII. This reaction is carried out utilizing conventional akylation techniques. Any conventional method of alkylating the alpha carbon atom of an organic acid ester with an alkyl halide can be utilized to effect this conversion and produce the compound of formula VII. In the next step of the reaction, the compound of formula VII is coupled with the alkyne of formula VIII to produce the compound of formula IX. Any conventional method of coupling an alkyne to an aromatic iodide can be utilized to effect this conversion. In accordance with the preferred embodiment of this invention, the coupling is carried out in the presence of copper iodide catalyst utilizing an auxiliary catalyst at temperatures of from about 80° to 120° C. Any coupling catalyst system can be used with the preferred system being bis-triphenyl phosphine dichloro palladium and copper iodide. After coupling, the compound of formula IX is converted to the compound of formula X by hydrolyzing the $R^7$ protecting group from the compound of formula IX. Any conventional method of hydrolyzing an ester can be utilized to effect this conversion. In the next step of the process, the compound of formula X is condensed to the compound of formula XI to produce the compound of formula I. This condensing reaction can be carried out utilizing any of the conventional means of amide formation.

The compound of formula I has an asymmetric carbon atom through which the group —$CH_2R^3$ and the acid amide substituents are connected. In accordance with this invention, the preferred stereoconfiguration of this group is R.

If it is desired to produce the R or the S isomer of the compound of formula I, this compound can be separated into these isomers by any conventional chemical means. Among the preferred chemical means is to react the compound of formula X with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction.

In the resolution step, the compound of formula X is reacted with the optically active base in an inert organic solvent medium to produce salts of the optically active amine with both the R and S isomers of the compound of formula X. In the formation of these salts, temperatures and pressure are not critical and the salt formation can take place at room temperature and atmospheric pressure. The R and S salts can be separated by any conventional method such as fractional crystallization. After crystallization, each of the salts can be converted to the respective compounds of formula X in the R and S configuration by hydrolysis with an acid. Among the preferred acids are dilute aqueous acids, i.e., from about 0.001N to 2N aqueous acids, such as aqueous sulfuric or aqueous hydrochloric acid. The configuration of formula X which is produced by this method of resolution is carried out throughout the entire reaction scheme to produce the desired R or S isomer of formula I. The separation of R and S isomers can also be achieved using an enzymatic ester hydrolysis of any lower alkyl esters corresponding to the compound of the formula X (see for example, Ahmar, M.; Girard, C.; Bloch, R, *Tetrahedron Lett*, 1989, 7053), which results in the formation of corresponding chiral acid and chiral ester. The ester and the acid can be separated by any conventional method of separating an acid from an ester. The preferred method of resolution of racemates of the compounds of the formula X is via the formation of corresponding diastereomeric esters or amides. These diastereomeric esters or amides can be prepared by coupling the carboxylic acids of the formula X with a chiral alcohol, or a chiral amine. This reaction can be carried out using any conventional method of coupling a carboxylic acid with an alcohol or an amine. The corresponding diastereomers of compounds of the formula X can then be separated using any conventional separation methods. The resulting pure diastereomeric esters or amides can then be hydrolyzed to yield the corresponding pure R or S isomers. The hydrolysis reaction can be carried out using conventional known methods to hydrolyze an ester or an amide without racemization.

All of the compounds of formula I which include the compounds set forth in the Examples, activated glucokinase in vitro by the procedure of Example A. In this manner, they increase the flux of glucose metabolism which causes increased insulin secretion. Therefore, the compounds of formula I are glucokinase activators useful for increasing insulin secretion.

On the basis of their capability of activating glucokinase, the compounds of above formula I can be used as medicaments for the treatment of type II diabetes. Therefore, as mentioned earlier, medicaments containing a compound of formula I are also an object of the present invention, as is a process for the manufacture of such medicaments, which process comprises bringing one or more compounds of formula I and, if desired, one or more other therapeutically valuable substances into a galenical administration form, e.g. by combining a compound of formula I with a pharmaceutically acceptable carrier and/or adjuvant.

The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels or solutions; or parenterally, e.g. intravenously, intramuscularly, subcutaneously, intrathecally or transdermally, using for example injectable solutions. Furthermore, administration can be carried out sublingually or as an aerosol, for example in the form of a spray. For the preparation of tablets, coated tablets, dragées or hard gelatine capsules the compounds of the present invention may be admixed with pharmaceutically inert, inorganic or organic excipients. Examples of suitable excipients for tablets, dragees or hard gelatine capsules include lactose, maize starch or derivatives thereof, talc or stearic acid or salts thereof. Suitable excipients for use with soft gelatine capsules include for example vegetable oils, waxes, fats, semi-solid or liquid polyols etc.; according to the nature of the active ingredients it may however be the case that no excipient is needed at all for soft gelatine capsules. For the preparation of solutions and syrups, excipients which may be used include for example water, polyols, saccharose, invert sugar and glucose. For injectable solutions, excipients which may be used include for example water, alcohols, polyols, glycerine, and vegetable oils. For suppositories, and local or percutaneous application, excipients which may be used include for example natural or hardened oils, waxes, fats and semi-solid or liquid polyols. The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. As mentioned earlier, they may also contain other therapeutically valuable agents. It is a prerequisite that all adjuvants used in the manufacture of the preparations are non-toxic.

Preferred forms of use are intravenous, intramuscular or oral administration, most preferred is oral administration. The dosages in which the compounds of formula (I) are administered in effective amounts depend on the nature of the specific active ingredient, the age and the requirements of the patient and the mode of application. In general, dosages of about 1–100 mg/kg body weight per day come into consideration.

This invention will be better understood from the following examples, which are for purposes of illustration and are not intended to limit the invention defined in the claims which follow thereafter.

EXAMPLE 1

3-Cyclopentyl-2-(4-ethynyl-phenyl)-N-thiazol-2-yl-propionamide

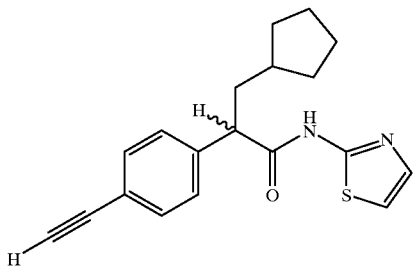

A solution of diisopropylamine (11.2 mL, 80.13 mmol) in tetrahydrofuran (120 mL) cooled to −78° C. was treated with a 2.5M solution of n-butyllithium in hexanes (32 mL, 80.13 mmol). This solution was stirred at −78° C. for 30 min and then treated with a solution of (4-iodo-phenyl)-acetic acid (9.67 g, 36.9 mmol) in tetrahydrofuran (88 mL) and 1,3-dimethyl-3,4,5,6-tetrahydro-2(1H)-pyrimidinone (29 mL). The reaction mixture was allowed to stir at −78° C. for 1 h. At this time, the reaction was treated with iodomethylcyclopentane (8.53 g, 40.6 mmol). The reaction mixture was allowed to slowly warm to 25° C. where it was stirred at 25° C. for 18 h. At this time, the reaction mixture was quenched with water (5 mL) and then concentrated in vacuo. The residue was diluted with water (800 mL) and then acidified to pH=2 with concentrated hydrochloric acid. This solution was extracted with ethyl acetate (2×800 mL). The combined organic extracts were washed with water (1×600 mL) and a saturated aqueous sodium chloride solution (1×600 mL), dried over sodium sulfate, filtered, and concentrated in vacuo. Flash chromatography (Merck Silica gel 60, 230–400 mesh, 50/50 hexanes/ethyl acetate) afforded 3-cyclopentyl-2-(4-iodo-phenyl)-propionic acid (7.34 g, 57.8%) as a white solid: mp 105–107° C.; EI-HRMS m/e calcd for $C_{14}H_{17}IO_2$ ($M^+$) 344.0273, found 344.0275.

A solution of 3-cyclopentyl-2-(4-iodo-phenyl)-propionic acid (7.18 g, 20.86 mmol) in methanol (150 mL) was treated with a catalytic amount of concentrated sulfuric acid (7 drops). The reaction mixture was heated at 70° C. for 18 h. At this time, the reaction was cooled to 25° C. and concentrated in vacuo. The residue was partitioned between ethyl acetate (400 mL) and a saturated aqueous sodium bicarbonate solution (400 mL). The aqueous layer was extracted with ethyl acetate (1×400 mL). The combined organic extracts were washed with a saturated aqueous sodium chloride solution (1×400 mL), dried over sodium sulfate, filtered, and concentrated in vacuo to afford 3-cyclopentyl-2-(4-iodo-phenyl)-propionic acid methyl ester (7.24 g, 96.9%) as an off-white solid: mp 51–54° C.; EI-HRMS m/e calcd for $C_{15}H_{19}IO_2$ ($M^+$) 358.0429, found 358.0419.

A solution of 3-cyclopentyl-2-(4-iodo-phenyl)-propionic acid methyl ester (716 mg, 2.0 mmol) and triethylamine (2 mL, 0.01 mmol) in N,N-dimethylformamide (2 mL) was treated with trimethylsilyl acetylene (0.71 mL, 5.0 mmol). The resulting reaction mixture was degassed with argon and then treated with cooper iodide (10 mg, 0.05 mmol) and bis(triphenylphosphine)palladium (II) chloride (15 mg, 0.02 mmol). The reaction was then heated at 70° C. for 24 h. At this time, the reaction was cooled to 25° C. and concentrated in vacuo. The residue was diluted with ethyl acetate (40 mL) and washed with a half-saturated aqueous sodium chloride solution (1×20 mL). The resulting aqueous layer was back extracted with ethyl acetate (1×40 mL). The combined organic extracts were dried over sodium sulfate, filtered, and concentrated in vacuo. Flash chromatography (Merck Silica gel 60, 230–400 mesh, 60/40 hexanes/ethyl acetate) afforded 3-cyclopentyl-2-(4-trimethylsilanylethynyl-phenyl)-propionic acid methyl ester (615 mg, 93.6%) as an orange solid: mp 72–74° C.; EI-HRMS m/e calcd for $C_{20}H_{28}O_2Si$ ($M^+$) 328.1858, found 328.1852.

A solution of 3-cyclopentyl-2-(4-trimethylsilanylethynyl-phenyl)-propionic acid methyl ester (600 mg, 1.83 mmol) in methanol (10 mL) and water (10 mL) was treated with lithium hydroxide (877 mg, 20.9 mmol). The reaction mixture was stirred at 25° C. for 18 h. At this time, the reaction was concentrated in vacuo. The residue was re-dissolved in water (40 mL) which was then acidified to pH=2 with concentrated hydrochloric acid. This solution was extracted with ethyl acetate (2×40 mL). The combined organic extracts were washed with a half-saturated aqueous sodium chloride solution (1×40 mL), dried over sodium sulfate, filtered, and concentrated in vacuo to afford 3-cyclopentyl-2-(4-ethynyl-phenyl)-propionic acid (448 mg, 100%) as a tan solid: mp 80–83° C.; EI-HRMS m/e calcd for $C_{16}H_{18}O_2$ ($M^+$) 242.1306, found 242.1309.

A solution of 3-cyclopentyl-2-(4-ethynyl-phenyl)-propionic acid (121 mg, 0.50 mmol), benzotriazol-1-yloxytris(dimethylamino)phosphonium hexafluorophosphate (332 mg, 0.75 mmol), triethylamine (0.21 mL, 1.50 mmol) and 2-aminothiazole (86 mg, 0.75 mmol) in methylene chloride (5 mL) was stirred at 25° C. for 24 h. At this time, the reaction was diluted with methylene chloride (10 mL). This solution was washed with water (1×10 mL), a 1N aqueous sodium hydroxide solution (1×10 mL), a 1N aqueous hydrochloric acid solution (1×10 mL), and a saturated aqueous sodium chloride solution (1×10 mL). The aqueous layers were back extracted with methylene chloride (1×10 mL). The combined organic extracts were dried over sodium sulfate, filtered, and concentrated in vacuo. Flash chromatography (Merck Silica gel 60, 230–400 mesh, 60/40 hexanes/ethyl acetate) afforded 3-cyclopentyl-2-(4-ethynyl-phenyl)-N-thiazol-2-yl-propionamide (92 mg, 56.8%) as a white solid: mp 181–183° C.; EI-HRMS m/e calcd for $C_{19}H_{20}N_2OS$ ($M^+$) 324.1296, found 324.1295.

EXAMPLE 2

3-Cyclopentyl-2-[4-(1-hydroxy-cyclohexylethynyl)-phenyl]-N-thiazol-2-yl-propionamide

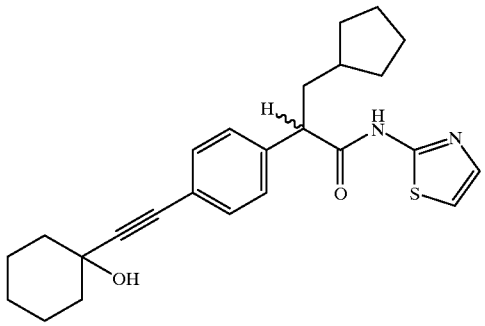

A solution of diisopropylamine (11.2 mL, 80.13 mmol) in tetrahydrofuran (120 mL) cooled to −78° C. was treated with a 2.5M solution of n-butyllithium in hexanes (32 mL, 80.13 mmol). This solution was stirred at −78° C. for 30 min and then treated with a solution of (4-iodo-phenyl)-acetic acid (9.67 g, 36.9 mmol) in tetrahydrofuran (88 mL) and 1,3-dimethyl-3,4,5,6-tetrahydro-2(1H)-pyrimidinone (29 mL). The reaction mixture was allowed to stir at −78° C. for 1 h. At this time, the reaction was treated with iodomethylcyclopentane (8.53 g, 40.6 mmol). The reaction mixture was allowed to slowly warm to 25° C. where it was stirred at 25° C. for 18 h. At this time, the reaction mixture was quenched with water (5 mL) and then concentrated in vacuo. The residue was diluted with water (800 mL) and then acidified to pH=2 with concentrated hydrochloric acid. This solution was extracted with ethyl acetate (2×800 mL). The combined organic extracts were washed with water (1×600 mL) and a saturated aqueous sodium chloride solution (1×600 mL), dried over sodium sulfate, filtered, and concentrated in vacuo. Flash chromatography (Merck Silica gel 60, 230–400 mesh, 50/50 hexanes/ethyl acetate) afforded 3-cyclopentyl-2-(4-iodo-phenyl)-propionic acid (7.34 g, 57.8%) as a white solid: mp 105–107° C.; EI-HRMS m/e calcd for $C_{14}H_{17}IO_2$ ($M^+$) 344.0273, found 344.0275.

A solution of 3-cyclopentyl-2-(4-iodo-phenyl)-propionic acid (7.18 g, 20.86 mmol) in methanol (150 mL) was treated with a catalytic amount of concentrated sulfuric acid (7 drops). The reaction mixture was heated at 70° C. for 18 h. At this time, the reaction was cooled to 25° C. and concentrated in vacuo. The residue was partitioned between ethyl acetate (400 mL) and a saturated aqueous sodium bicarbonate solution (400 mL). The aqueous layer was extracted with ethyl acetate (1×400 mL). The combined organic extracts were washed with a saturated aqueous sodium chloride solution (1×400 mL), dried over sodium sulfate, filtered, and concentrated in vacuo to afford 3-cyclopentyl-2-(4-iodo-phenyl)-propionic acid methyl ester (7.24 g, 96.9%) as an off-white solid: mp 51–54° C.; EI-HRMS m/e calcd for $C_{15}H_{19}IO_2$ ($M^+$) 358.0429, found 358.0419.

A solution of 3-cyclopentyl-2-(4-iodo-phenyl)-propionic acid methyl ester (716 mg, 2.0 mmol) and triethylamine (2 mL, 0.01 mmol) in N,N-dimethylformamide (2 mL) was treated with 1-ethynyl cyclohexanol (621 mg, 5.0 mmol). The resulting reaction mixture was degassed with argon and then treated with cooper iodide (10 mg, 0.05 mmol) and bis(triphenylphosphine)palladium (II) chloride (15 mg, 0.02 mmol). The reaction was then heated at 70° C. for 24 h. At this time, the reaction was cooled to 25° C. and concentrated in vacuo. The residue was diluted with ethyl acetate (40 mL) and then washed with a half-saturated aqueous sodium chloride solution (1×20 mL). The aqueous layer was back extracted with ethyl acetate (1×40 mL). The combined organic extracts were dried over sodium sulfate, filtered, and concentrated in vacuo. Flash chromatography (Merck Silica gel 60, 230–400 mesh, 60/40 ethyl acetate/hexanes) afforded 3-cyclopentyl-2-[4-(1-hydroxy-cyclohexylethynyl)-phenyl]-propionic acid methyl ester (774 mg, 98%) as a cream solid: mp 76–78° C.; EI-HRMS m/e calcd for $C_{23}H_{30}O_3$ ($M^+$) 354.2194, found 354.2194.

A solution of 3-cyclopentyl-2-[4-(1-hydroxy-cyclohexylethynyl)-phenyl]-propionic acid methyl ester (753 mg, 2.0 mmol) in methanol (10 mL) and water (10 mL) was treated with lithium hydroxide (1.02 g, 24.3 mmol). The reaction mixture was stirred at 25° C. for 18 h. At this time, the reaction was concentrated in vacuo. The residue was diluted with water (40 mL). This solution was acidified to pH=2 with concentrated hydrochloric acid and then extracted with ethyl acetate (2×40 mL). The combined organic extracts were then washed with a half-saturated sodium chloride solution (1×40 mL), dried over sodium sulfate, filtered, and concentrated in vacuo to afford 3-cyclopentyl-2-[4-(1-hydroxy-cyclohexylethynyl)-phenyl]-propionic acid (727 mg, quant.) as an amber foam: EI-HRMS m/e calcd for $C_{22}H_{28}O_3$ ($M^+$) 340.2038, found 340.2037.

A solution of 3-cyclopentyl-2-[4-(1-hydroxy-cyclohexylethynyl)-phenyl]-propionic acid (170 mg, 0.50 mmol), benzotriazol-1-yloxytris(dimethylamino) phosphonium hexafluorophosphate (332 mg, 0.75 mmol), triethylamine (0.21 mL, 1.50 mmol) and 2-aminothiazole (86 mg, 0.75 mmol) in methylene chloride (5 mL) was stirred at 25° C. for 4 h. At this time, the reaction was diluted with methylene chloride (10 mL). This solution was washed with water (1×10 mL), a 1N aqueous sodium hydroxide solution (1×10 mL), a 1N aqueous hydrochloric acid solution (1×10 mL), and a half-saturated aqueous sodium chloride solution (1×10 mL). The aqueous layers were back extracted with methylene chloride (1×10 mL). The combined organic extracts were dried over sodium sulfate, filtered, and concentrated in vacuo. Flash chromatography (Merck Silica gel 60, 230–400 mesh, 50/50 hexanes/ethyl acetate) afforded 3-cyclopentyl-2-[4-(1-hydroxy-cyclohexylethynyl)-phenyl]-N-thiazol-2-yl-propionamide (123 mg, 58.3%) as a white solid: mp 172–173° C.; EI-HRMS m/e calcd for $C_{25}H_{30}N_2O_2S$ ($M^+$) 422.2028, found 422.2023.

EXAMPLE 3

3-Cyclopentyl-2-[4-(3-methoxy-prop-1-ynyl)-phenyl]-N-thiazol-2-yl-propionamide

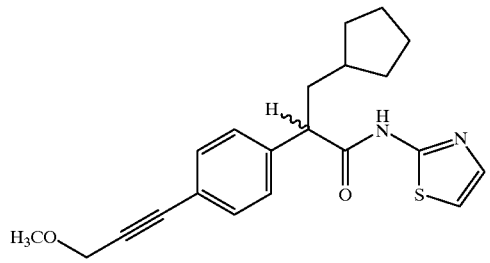

A solution of diisopropylamine (11.2 mL, 80.13 mmol) in tetrahydrofuran (120 mL) cooled to −78° C. was treated with a 2.5M solution of n-butyllithium in hexanes (32 mL, 80.13 mmol). This solution was stirred at −78° C. for 30 min and then treated with a solution of (4-iodo-phenyl)-acetic acid (9.67 g, 36.9 mmol) in tetrahydrofuran (88 mL) and 1,3-dimethyl-3,4,5,6-tetrahydro-2(1H)-pyrimidinone (29 mL). The reaction mixture was allowed to stir at −78° C. for 1 h. At this time, the reaction was treated with iodomethylcyclopentane (8.53 g, 40.6 mmol). The reaction mixture was allowed to slowly warm to 25° C. where it was stirred at 25° C. for 18 h. At this time, the reaction mixture was quenched with water (5 mL) and then concentrated in vacuo. The residue was diluted with water (800 mL) and then acidified to pH=2 with concentrated hydrochloric acid. This solution was extracted with ethyl acetate (2×800 mL). The combined organic extracts were washed with water (1×600 mL) and a saturated aqueous sodium chloride solution (1×600 mL), dried over sodium sulfate, filtered, and concentrated in vacuo. Flash chromatography (Merck Silica gel 60, 230-400 mesh, 50/50 hexanes/ethyl acetate) afforded 3-cyclopentyl-2-(4-iodo-phenyl)-propionic acid (7.34 g, 57.8%) as a white solid: mp 105–107° C.; EI-HRMS m/e calcd for $C_{14}H_{17}IO_2$ (M$^+$) 344.0273, found 344.0275.

A solution of 3-cyclopentyl-2-(4-iodo-phenyl)-propionic acid (7.18 g, 20.86 mmol) in methanol (150 mL) was treated with a catalytic amount of concentrated sulfuric acid (7 drops). The reaction mixture was heated at 70° C. for 18 h. At this time, the reaction was cooled to 25° C. and concentrated in vacuo. The residue was partitioned between ethyl acetate (400 mL) and a saturated aqueous sodium bicarbonate solution (400 mL). The aqueous layer was extracted with ethyl acetate (1×400 mL). The combined organic extracts were washed with a saturated aqueous sodium chloride solution (1×400 mL), dried over sodium sulfate, filtered, and concentrated in vacuo to afford 3-cyclopentyl-2-(4-iodo-phenyl)-propionic acid methyl ester (7.24 g, 96.9%) as an off-white solid: mp 51–54° C.; EI-HRMS m/e calcd for $C_{15}H_{19}IO_2$ (M$^+$) 358.0429, found 358.0419.

A solution of 3-cyclopentyl-2-(4-iodo-phenyl)-propionic acid methyl ester (716 mg, 2.0 mmol) and triethylamine (2 mL, 0.01 mmol) in N,N-dimethylformamide (2 mL) was treated with methyl propargyl ether (0.71 mL, 5.0 mmol). The resulting reaction mixture was degassed with argon and then treated with cooper iodide (10 mg, 0.05 mmol) and bis(triphenylphosphine)palladium (II) chloride (15 mg, 0.02 mmol). The reaction was then heated at 70° C. for 24 h. At this time, the reaction was cooled to 25° C. and concentrated in vacuo. The residue was diluted with ethyl acetate (40 mL) and washed with a half-saturated aqueous sodium chloride solution (1×20 mL). The resulting aqueous layer was back extracted with ethyl acetate (1×40 mL). The combined organic extracts were dried over sodium sulfate, filtered, and concentrated in vacuo. Flash chromatography (Merck Silica gel 60, 230-400 mesh, 85/15 hexanes/ethyl acetate) afforded 3-cyclopentyl-2-[4-(3-methoxy-prop-1-ynyl)-phenyl]-propionic acid methyl ester (503 mg, 83.8%) as an amber oil: EI-HRMS m/e calcd for $C_{19}H_{24}O_3$ (M$^+$) 300.1725, found 300.1728.

A solution of 3-cyclopentyl-2-[4-(3-methoxy-prop-1-ynyl)-phenyl]-propionic acid methyl ester (485 mg, 1.61 mmol) in tetrahydrofuran (10 mL) and water (10 mL) was treated with lithium hydroxide (775 mg, 18.5 mmol). The reaction mixture was stirred at 25° C. for 48 h. At this time, the reaction was concentrated in vacuo. The residue was re-dissolved in water (40 mL) which was then acidified to pH=2 with concentrated hydrochloric acid. This solution was extracted with ethyl acetate (2×40 mL). The aqueous layers were back extracted with ethyl acetate (1×40 mL). The combined organic extracts were then washed with a half-saturated aqueous sodium chloride solution (1×40 mL), dried over sodium sulfate, filtered, and concentrated in vacuo to afford 3-cyclopentyl-2-[4-(3-methoxy-prop-1-ynyl)-phenyl]-propionic acid (447 mg, 96.7%) as a white solid: mp 82–85° C.; EI-HRMS m/e calcd for $C_{18}H_{22}O_3$ (M$^+$) 286.1568, found 286.1563.

A solution of 3-cyclopentyl-2-[4-(3-methoxy-prop-1-ynyl)-phenyl]-propionic acid (143 mg, 0.50 mmol), benzotriazol-1-yloxytris(dimethylamino)phosphonium hexafluorophosphate (332 mg, 0.75 mmol), triethylamine (0.21 mL, 1.50 mmol) and 2-aminothiazole (75 mg, 0.75 mmol) in methylene chloride (5 mL) was stirred at 25° C. for 24 h. At this time, the reaction was diluted with methylene chloride (5 mL). This solution was washed with water (1×10 mL), a 1N aqueous sodium hydroxide solution (1×10 mL), a 1N aqueous hydrochloric acid solution (1×10 mL), and a saturated aqueous sodium chloride solution (1×10 mL). The aqueous layers were back extracted with methylene chloride (1×10 mL). The combined organic extracts were dried over sodium sulfate, filtered, and concentrated in vacuo. Flash chromatography (Merck Silica gel 60, 230–400 mesh, 60/40 hexanes/ethyl acetate) afforded 3-cyclopentyl-2-[4-(3-methoxy-prop-1-ynyl)-phenyl]-N-thiazol-2-yl-propionamide (133 mg, 72%) as a white solid: mp 170–172° C.; EI-HRMS m/e calcd for $C_{21}H_{24}N_2O_2S$ (M$^+$) 368.1558, found 368.1556.

In an analogous manner, there was obtained:

(a) From 3-cyclopentyl-2-[4-(3-methoxy-prop-1-ynyl)-phenyl]-propionic acid and ethyl 2-amino-5-thiazolecarboxylate: 2-{3-cyclopentyl-2-[4-(3-methoxy-prop-1-ynyl)-phenyl]-propionylamino}-thiazole-4-carboxylic acid ethyl ester as a white foam: EI-HRMS m/e calcd for $C_{24}H_{28}N_2O_4S$ (M$^+$) 440.1770, found 440.1761.

EXAMPLE 4

3-Cyclopentyl-2-[4-(3-hydroxy-3-methyl-pent-1-ynyl)-phenyl]-N-thiazol-2-yl-propionamide

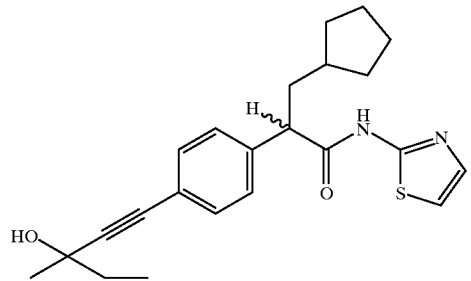

A solution of diisopropylamine (11.2 mL, 80.13 mmol) in tetrahydrofuran (120 mL) cooled to −78° C. was treated with a 2.5M solution of n-butyllithium in hexanes (32 mL, 80.13 mmol). This solution was stirred at −78° C. for 30 min and then treated with a solution of (4-iodo-phenyl)-acetic acid (9.67 g, 36.9 mmol) in tetrahydrofuran (88 mL) and 1,3-dimethyl-3,4,5,6-tetrahydro-2(1H)-pyrimidinone (29 mL). The reaction mixture was allowed to stir at −78° C. for 1 h. At this time, the reaction was treated with iodomethylcyclopentane (8.53 g, 40.6 mmol). The reaction mixture was allowed to slowly warm to 25° C. where it was stirred at 25° C. for 18 h. At this time, the reaction mixture was quenched with water (5 mL) and then concentrated in vacuo. The residue was diluted with water (800 mL) and was acidified to pH=2 with concentrated hydrochloric acid. This solution was extracted with ethyl acetate (2×800 mL). The combined organic extracts were washed with water (1×600 mL) and a saturated aqueous sodium chloride solution (1×600 mL), dried over sodium sulfate, filtered, and concentrated in vacuo. Flash chromatography (Merck Silica gel 60, 230–400 mesh, 50/50 hexanes/ethyl acetate) afforded 3-cyclopentyl-2-(4-iodo-phenyl)-propionic acid (7.34 g, 57.8%) as a white solid: mp 105–107° C.; EI-HRMS m/e calcd for $C_{14}H_{17}IO_2$ ($M^+$) 344.0273, found 344.0275.

A solution of 3-cyclopentyl-2-(4-iodo-phenyl)-propionic acid (7.18 g, 20.86 mmol) in methanol (150 mL) was treated with a catalytic amount of concentrated sulfuric acid (7 drops). The reaction mixture was heated at 70° C. for 18 h. At this time, the reaction was cooled to 25° C. and concentrated in vacuo. The residue was partitioned between ethyl acetate (400 mL) and a saturated aqueous sodium bicarbonate solution (400 mL). The aqueous layer was extracted with ethyl acetate (1×400 mL). The combined organic extracts were washed with a saturated aqueous sodium chloride solution (1×400 mL), dried over sodium sulfate, filtered, and concentrated in vacuo to afford 3-cyclopentyl-2-(4-iodo-phenyl)-propionic acid methyl ester (7.24 g, 96.9%) as an off-white solid: mp 51–54° C.; EI-HRMS m/e calcd for $C_{15}H_{19}IO_2$ ($M^+$) 358.0429, found 358.0419.

A solution of 3-cyclopentyl-2-(4-iodo-phenyl)-propionic acid methyl ester (716 mg, 2.0 mmol) and triethylamine (2 mL, 0.01 mmol) in N,N-dimethylformamide (2 mL) was treated with 3-methyl-1-pentyn-3-ol (0.56 mL, 5.0 mmol). The resulting reaction mixture was degassed with argon and then treated with cooper iodide (10 mg, 0.05 mmol) and bis(triphenylphosphine)palladium (II) chloride (15 mg, 0.02 mmol). The reaction was then heated at 70° C. for 24 h. At this time, the reaction was cooled to 25° C. and concentrated in vacuo. The residue was diluted with ethyl acetate (40 mL) and a half-saturated aqueous sodium chloride solution (1×20 mL). The aqueous layer was back extracted with ethyl acetate (1×40 mL). The combined organic extracts were washed with a half-saturated aqueous sodium chloride solution (1×20 mL), dried over sodium sulfate, filtered, and concentrated in vacuo. Flash chromatography (Merck Silica gel 60, 230–400 mesh, 60/40 ethyl acetate/hexanes) afforded 3-cyclopentyl-2-[4-(3-hydroxy-3-methyl-pent-1-ynyl)-phenyl]-propionic acid methyl ester (673 mg, 98%) as an orange oil: EI-HRMS m/e calcd for $C_{21}H_{28}O_3$ ($M^+$) 328.2038, found 328.2040.

A solution of 3-cyclopentyl-2-[4-(3-hydroxy-3-methyl-pent-1-ynyl)-phenyl]-propionic acid methyl ester (656 mg, 1.99 mmol) in methanol (10 mL) and water (10 mL) was treated with lithium hydroxide (920 mg, 21.9 mmol). The reaction mixture was stirred at 25° C. for 18 h. At this time, the reaction was concentrated in vacuo. The residue was diluted with water (40 mL). This solution was acidified to pH=2 with concentrated hydrochloric acid and then extracted with ethyl acetate (2×40 mL). The combined organic extracts were then washed with a half-saturated sodium chloride solution (1×40 mL), dried over sodium sulfate, filtered, and concentrated in vacuo to afford 3-cyclopentyl-2-[4-(3-hydroxy-3-methyl-pent-1-ynyl)-phenyl]-propionic acid (570 mg, 91%) as a tan solid: mp 91–94° C.; EI-HRMS m/e calcd for $C_{20}H_{26}O_3$ ($M^+$) 314.1881, found 314.1872.

A solution of 3-cyclopentyl-2-[4-(3-hydroxy-3-methyl-pent-1-ynyl)-phenyl]-propionic acid (157 mg, 0.50 mmol), benzotriazol-1-yloxytris(dimethylamino)phosphonium hexafluorophosphate (332 mg, 0.75 mmol), triethylamine (0.21 mL, 1.50 mmol) and 2-aminothiazole (86 mg, 0.75 mmol) in methylene chloride (5 mL) was stirred at 25° C. for 2 h. At this time, the reaction was diluted with methylene chloride (10 mL). This solution was washed with water (1×10 mL), a 1N aqueous sodium hydroxide solution (1×10 mL), a 1N aqueous hydrochloric acid solution (1×10 mL), and a half-saturated aqueous sodium chloride solution (1×10 mL). The aqueous layers were back extracted with methylene chloride (1×10 mL). The combined organic extracts were dried over sodium sulfate, filtered, and concentrated in vacuo. Flash chromatography (Merck Silica gel 60, 230–400 mesh, 50/50 hexanes/ethyl acetate) afforded 3-cyclopentyl-2-[4-(3-hydroxy-3-methyl-pent-1-ynyl)-phenyl]-N-thiazol-2-yl-propionamide (113 mg, 57.1%) as a white solid: mp 172–174° C.; EI-HRMS m/e calcd for $C_{23}H_{28}N_2O_2S$ ($M^+$) 396.1871, found 396.1866.

EXAMPLE 5

3-Cyclopentyl-2-[4-(4-hydroxy-pent-1-ynyl)-phenyl]-N-thiazol-2-yl-propionamide

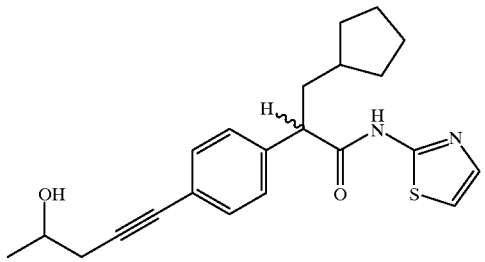

A solution of diisopropylamine (11.2 mL, 80.13 mmol) in tetrahydrofuran (120 mL) cooled to −78° C. was treated with a 2.5M solution of n-butyllithium in hexanes (32 mL, 80.13 mmol). This solution was stirred at −78° C. for 30 min and then treated with a solution of (4-iodo-phenyl)-acetic acid (9.67 g, 36.9 mmol) in tetrahydrofuran (88 mL) and 1,3-dimethyl-3,4,5,6-tetrahydro-2(1H)-pyrimidinone (29 mL). The reaction mixture was allowed to stir at −78° C. for 1 h. At this time, the reaction was treated with iodomethylcyclopentane (8.53 g, 40.6 mmol). The reaction mixture was allowed to slowly warm to 25° C. where it was stirred at 25° C. for 18 h. At this time, the reaction mixture was quenched with water (5 mL) and then concentrated in vacuo. The residue was diluted with water (800 mL) and was acidified to pH=2 with concentrated hydrochloric acid. This solution was extracted with ethyl acetate (2×800 mL). The combined organic extracts were washed with water (1×600 mL) and a saturated aqueous sodium chloride solution (1×600 mL), dried over sodium sulfate, filtered, and concentrated in vacuo. Flash chromatography (Merck Silica gel 60, 230–400 mesh, 50/50 hexanes/ethyl acetate) afforded 3-cyclopentyl-2-(4-iodo-phenyl)-propionic acid (7.34 g, 57.8%) as a white solid: mp 105–107° C.; EI-HRMS m/e calcd for $C_{14}H_{17}IO_2$ ($M^+$) 344.0273, found 344.0275.

A solution of 3-cyclopentyl-2-(4-iodo-phenyl)-propionic acid (7.18 g, 20.86 mmol) in methanol (150 mL) was treated with a catalytic amount of concentrated sulfuric acid (7 drops). The reaction mixture was heated at 70° C. for 18 h. At this time, the reaction was cooled to 25° C. and concentrated in vacuo. The residue was partitioned between ethyl acetate (400 mL) and a saturated aqueous sodium bicarbonate solution (400 mL). The aqueous layer was extracted with ethyl acetate (1×400 mL). The combined organic extracts were washed with a saturated aqueous sodium chloride solution (1×400 mL), dried over sodium sulfate, filtered, and concentrated in vacuo to afford 3-cyclopentyl-2-(4-iodo-phenyl)-propionic acid methyl ester (7.24 g, 96.9%) as an off-white solid: mp 51–54° C.; EI-HRMS m/e calcd for $C_{15}H_{19}IO_2$ (M⁺) 358.0429, found 358.0419.

A solution of 3-cyclopentyl-2-(4-iodo-phenyl)-propionic acid methyl ester (716 mg, 2.0 mmol) and triethylamine (2 mL, 0.01 mmol) in N,N-dimethylformamide (2 mL) was treated with 4-pentyne-2-ol (0.47 mL, 5.0 mmol). The resulting reaction mixture was degassed with argon and then treated with cooper iodide (10 mg, 0.05 mmol) and bis(triphenylphosphine)palladium (II) chloride (15 mg, 0.02 mmol). The reaction was then heated at 70° C. for 24 h. At this time, the reaction was cooled to 25° C. and concentrated in vacuo. The residue was diluted with ethyl acetate (40 mL) and a half-saturated aqueous sodium chloride solution (1×20 mL). The aqueous layer was back extracted with ethyl acetate (1×40 mL). The combined organic extracts were washed with a half-saturated aqueous sodium chloride solution (1×20 mL), dried over sodium sulfate, filtered, and concentrated in vacuo. Flash chromatography (Merck Silica gel 60, 230–400 mesh, 60/40 ethyl acetate/hexanes) afforded 3-cyclopentyl-2-[4-(4-hydroxy-pent-1-ynyl)-phenyl]-propionic acid methyl ester (578 mg, 92%) as an amber oil: EI-HRMS m/e calcd for $C_{20}H_{26}O_3$ (M⁺) 314.1881, found 314.1888.

A solution of 3-cyclopentyl-2-[4-(4-hydroxy-pent-1-ynyl)-phenyl]-propionic acid methyl ester (545 mg, 1.73 mmol) in tetrahydrofuran (10 mL) and water (10 mL) was treated with lithium hydroxide (830 mg, 19.8 mmol). The reaction mixture was stirred at 25° C. for 3 d. At this time, the reaction was concentrated in vacuo. The residue was diluted with water (40 mL). This solution was acidified to pH=2 with concentrated hydrochloric acid and then extracted with ethyl acetate (2×40 mL). The combined organic extracts were then washed with a half-saturated sodium chloride solution (1×40 mL), dried over sodium sulfate, filtered and concentrated in vacuo to afford 3-cyclopentyl-2-[4-(4-hydroxy-pent-1-ynyl)-phenyl]-propionic acid (565 mg, quant.) as a light brown solid: mp 73–76° C.; EI-HRMS m/e calcd for $C_{19}H_{24}O_3$ (M) 300.1725, found 300.1724.

A solution of 3-cyclopentyl-2-[4-(4-hydroxy-pent-1-ynyl)-phenyl]-propionic acid (100 mg, 0.30 mmol), benzotriazol-I -yloxytris(dimethylamino)phosphonium hexafluorophosphate (200 mg, 0.45 mmol), triethylamine (0.13 mL, 0.93 mmol) and 2-aminothiazole (52 mg, 0.45 mmol) in methylene chloride (5 mL) was stirred at 25° C. for 2 h. At this time, the reaction was diluted with methylene chloride (10 mL). This solution was washed with water (1×10 mL), a 1N aqueous sodium hydroxide solution (1×10 mL), a 1N aqueous hydrochloric acid solution (1×10 mL), and a half-saturated aqueous sodium chloride solution (1×10 mL). The aqueous layers were back extracted with methylene chloride (1×10 mL). The combined organic extracts were dried over sodium sulfate, filtered, and concentrated in vacuo. Flash chromatography (Merck Silica gel 60, 230–400 mesh, 60/40 hexanes/ethyl acetate) afforded 3-cyclopentyl-2-[4-(4-hydroxy-pent-1-ynyl)-phenyl]-N-thiazol-2-yl-propionamide (61 mg, 47.9%) as a white solid: mp 162–163° C.; EI-HRMS m/e calcd for $C_{22}H_{26}N_2O_2S$ (M⁺) 382.1715, found 382.1718.

EXAMPLE 6

3-Cyclopentyl-2-[4-(3-hydroxy-prop-1-ynyl)-phenyl]-N-thiazol-2-yl-propionamide

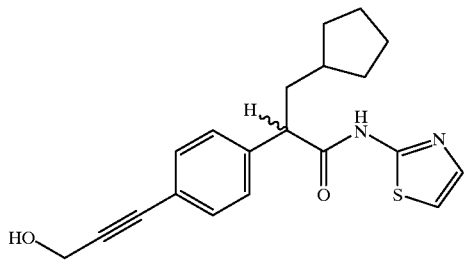

A solution of diisopropylamine (11.2 mL, 80.13 mmol) in tetrahydrofuran (120 mL) cooled to −78° C. was treated with a 2.5M solution of n-butyllithium in hexanes (32 mL, 80.13 mmol). This solution was stirred at −78° C. for 30 min and then treated with a solution of (4-iodo-phenyl)-acetic acid (9.67 g, 36.9 mmol) in tetrahydrofuran (88 mL) and 1,3-dimethyl-3,4,5,6-tetrahydro-2(1H)-pyrimidinone (29 mL). The reaction mixture was allowed to stir at −78° C. for 1 h. At this time, the reaction was treated with iodomethylcyclopentane (8.53 g, 40.6 mmol). The reaction mixture was allowed to slowly warm to 25° C. where it was stirred at 25° C. for 18 h. At this time, the reaction mixture was quenched with water (5 mL) and then concentrated in vacuo. The residue was diluted with water (800 mL) and then acidified to pH=2 with concentrated hydrochloric acid. This solution was extracted with ethyl acetate (2×800 mL). The combined organic extracts were washed with water (1×600 mL) and a saturated aqueous sodium chloride solution (1×600 mL), dried over sodium sulfate, filtered, and concentrated in vacuo. Flash chromatography (Merck Silica gel 60, 230–400 mesh, 50/50 hexanes/ethyl acetate) afforded 3-cyclopentyl-2-(4-iodo-phenyl)-propionic acid (7.34 g, 57.8%) as a white solid: mp 105–107° C.; EI-HRMS m/e calcd for $C_{14}H_{17}IO_2$ (M⁺) 344.0273, found 344.0275.

A solution of 3-cyclopentyl-2-(4-iodo-phenyl)-propionic acid (7.18 g, 20.86 mmol) in methanol (150 mL) was treated with a catalytic amount of concentrated sulfuric acid (7 drops). The reaction mixture was heated at 70° C. for 18 h. At this time, the reaction was cooled to 25° C. and concentrated in vacuo. The residue was partitioned between ethyl acetate (400 mL) and a saturated aqueous sodium bicarbonate solution (400 mL). The aqueous layer was extracted with ethyl acetate (1×400 mL). The combined organic extracts were washed with a saturated aqueous sodium chloride solution (1×400 mL), dried over sodium sulfate, filtered, and concentrated in vacuo to afford 3-cyclopentyl-2-(4-iodo-phenyl)-propionic acid methyl ester (7.24 g, 96.9%) as an off-white solid: mp 51–54° C.; EI-HRMS m/e calcd for $C_{15}H_{19}IO_2$ (M⁺) 358.0429, found 358.0419.

A solution of 3-cyclopentyl-2-(4-iodo-phenyl)-propionic acid methyl ester (2.15 g, 6.00 mmol) and triethylamine (6 mL, 0.04 mmol) in N,N-dimethylformamide (6 mL) was treated with propargyl alcohol (0.87 mL, 15.0 mmol). The resulting reaction mixture was degassed with argon and then treated with cooper iodide (30 mg, 0.15 mmol) and bis(triphenylphosphine)palladium (II) chloride (45 mg, 0.06 mmol). The reaction was then heated at 70° C. for 24 h. At this time, the reaction was cooled to 25° C. and concentrated in vacuo. The residue was diluted with ethyl acetate (120 mL) and washed with a half-saturated aqueous sodium chloride solution (1×60 mL). The resulting aqueous layer was back extracted with ethyl acetate (1×120 mL). The combined organic extracts were dried over sodium sulfate, filtered, and concentrated in vacuo. Flash chromatography (Merck Silica gel 60, 230–400 mesh, 60/40 hexanes/ethyl acetate) afforded 3-cyclopentyl-2-[4-(3-hydroxy-prop-1-ynyl)-phenyl]-propionic acid methyl ester (1.57 g, 91%) as an amber oil.

A solution of 3-cyclopentyl-2-[4-(3-hydroxy-prop-1-ynyl)-phenyl]-propionic acid methyl ester (1.55 g, 5.41 mmol) in methanol (30 mL) and water (30 mL) was treated with lithium hydroxide (2.60 g, 61.9 mmol). The reaction mixture was stirred at 25° C. for 48 h. At this time, the reaction was concentrated in vacuo. The residue was re-dissolved in water (100 mL) which was then acidified to pH=2 with concentrated hydrochloric acid. This solution was extracted with ethyl acetate (2×120 mL). The combined organic extracts were then washed with a half-saturated aqueous sodium chloride solution (1×40 mL), dried over sodium sulfate, filtered, and concentrated in vacuo to afford 3-cyclopentyl-2-[4-(3-hydroxy-prop-1-ynyl)-phenyl]-propionic acid (1.27 g, 86%) as an off-white solid.

A solution of 3-cyclopentyl-2-[4-(3-hydroxy-prop-1-ynyl)-phenyl]-propionic acid (380 mg, 1.4 mmol), in methylene chloride (4 mL) and N,N-dimethylformamide (1 drop) at 0° C. was treated with oxalyl chloride (1.22 mL, 14.0 mmol). The reaction was warmed to 25° C. and stirred at 25° C. for 18 h. At this time, the reaction mixture was concentrated in vacuo. The resulting residue was dissolved in methylene chloride (4 mL) and added to a solution of 2-aminothiazole (280 mg, 2.79 mmol) and N,N-diisopropylethylamine (0.50 mL, 2.87 mmol) in methylene chloride (8 mL) at 25° C. The reaction was stirred at 25° C. for 18 h. At this time, the reaction was concentrated in vacuo. The residue was poured into a 0.5N aqueous hydrochloric acid solution (50 mL) and extracted into ethyl acetate (1×100 mL). The organic extract was washed with a saturated aqueous sodium bicarbonate solution (1×50 mL) and a half-saturated aqueous sodium chloride solution (1×50 mL). The aqueous layer was back extracted with ethyl acetate (1×100 mL). The combined organic extracts were dried over sodium sulfate, filtered, and concentrated in vacuo. Flash chromatography (Merck Silica gel 60, 230–400 mesh, 60/40 hexanes/ethyl acetate) afforded the 3-cyclopentyl-2-[4-(3-hydroxy-prop-1-ynyl)-phenyl]-N-thiazol-2-yl-propionamide (159 mg, 72%) as an off-white solid: mp 220–222° C.; EI-HRMS m/e calcd for $C_{20}H_{22}N_2O_2S$ ($M^+$) 354.1402, found 354.1388.

EXAMPLE 7

3-Cyclopentyl-2-14-(3-dimethylamino-prop-1-ynyl)-phenyl)-N-thiazol-2-yl-propionamide

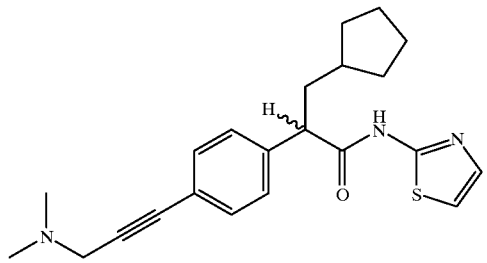

A solution of diisopropylamine (11.2 mL, 80.13 mmol) in tetrahydrofuran (120 mL) cooled to –78° C. was treated with a 2.5M solution of n-butyllithium in hexanes (32 mL, 80.13 mmol). This solution was stirred at –78° C. for 30 min and then treated with a solution of (4-iodo-phenyl)-acetic acid (9.67 g, 36.9 mmol) in tetrahydrofuran (88 mL) and 1,3-dimethyl-3,4,5,6-tetrahydro-2(1H)-pyrimidinone (29 mL). The reaction mixture was allowed to stir at –78° C. for 1 h. At this time, the reaction was treated with iodomethylcyclopentane (8.53 g, 40.6 mmol). The reaction mixture was allowed to slowly warm to 25° C. where it was stirred at 25° C. for 18 h. At this time, the reaction mixture was quenched with water (5 mL) and then concentrated in vacuo. The residue was diluted with water (800 mL) and then acidified to pH=2 with concentrated hydrochloric acid. This solution was extracted with ethyl acetate (2×800 mL). The combined organic extracts were washed with water (1×600 mL) and a saturated aqueous sodium chloride solution (1×600 mL), dried over sodium sulfate, filtered, and concentrated in vacuo. Flash chromatography (Merck Silica gel 60, 230–400 mesh, 50/50 hexanes/ethyl acetate) afforded 3-cyclopentyl-2-(4-iodo-phenyl)-propionic acid (7.34 g, 57.8%) as a white solid: mp 105–107° C.; EI-HRMS m/e calcd for $C_{14}H_{17}IO_2$ ($M^+$) 344.0273, found 344.0275.

A solution of 3-cyclopentyl-2-(4-iodo-phenyl)-propionic acid (7.18 g, 20.86 mmol) in methanol (150 mL) was treated with a catalytic amount of concentrated sulfuric acid (7 drops). The reaction mixture was heated at 70° C. for 18 h. At this time, the reaction was cooled to 25° C. and concentrated in vacuo. The residue was partitioned between ethyl acetate (400 mL) and a saturated aqueous sodium bicarbonate solution (400 mL). The aqueous layer was extracted with ethyl acetate (1×400 mL). The combined organic extracts were washed with a saturated aqueous sodium chloride solution (1×400 mL), dried over sodium sulfate, filtered, and concentrated in vacuo to afford 3-cyclopentyl-2-(4-iodo-phenyl)-propionic acid methyl ester (7.24 g, 96.9%) as an off-white solid: mp 51–54° C.; EI-HRMS m/e calcd for $C_{15}H_{19}IO_2$ ($M^+$) 358.0429, found 358.0419.

A solution of 3-cyclopentyl-2-(4-iodo-phenyl)-propionic acid methyl ester (716 mg, 2.0 mmol) and triethylamine (2 mL, 0.01 mmol) in N,N-dimethylformamide (2 mL) was treated with 1-dimethylamino-2-propyne (0.54 mL, 5.0 mmol). The resulting reaction mixture was degassed with argon and then treated with cooper iodide (10 mg, 0.05 mmol) and bis(triphenylphosphine)palladium (II) chloride (15 mg, 0.02 mmol). The reaction was then heated at 70° C. for 24 h. At this time, the reaction was cooled to 25° C. and concentrated in vacuo. The residue was diluted with ethyl acetate (40 mL) and washed with a half-saturated aqueous sodium chloride solution (1×20 mL). The resulting aqueous layer was back extracted with ethyl acetate (1×120 mL). The combined organic extracts were dried over sodium sulfate, filtered, and concentrated in vacuo. Flash chromatography (Merck Silica gel 60, 230–400 mesh, 95/5 chloroform/methanol) afforded 3-cyclopentyl-2-[4-(3-dimethylamino-prop-1-ynyl)-phenyl]-propionic acid methyl ester (572 mg, 91%) as an amber oil: EI-HRMS m/e calcd for $C_{20}H_{27}NO_3$ ($M^+$) 313.2051, found 312.1850.

A solution of 3-cyclopentyl-2-[4-(3-dimethylamino-prop-1-ynyl)-phenyl]-propionic acid methyl ester (563 mg, 1.80 mmol) in methanol (10 mL) and water (10 mL) was treated with lithium hydroxide (862 mg, 20.5 mmol). The reaction mixture was stirred at 25° C. for 18 h. At this time, the reaction was concentrated in vacuo. The residue was diluted with water (40 mL). This solution was acidified to pH=5 with concentrated hydrochloric acid and then extracted with ethyl acetate (1×40 mL) and chloroform/methanol (3:2, 1×50 mL). The combined organic extracts were then dried over sodium sulfate, filtered, and concentrated in vacuo to afford 3-cyclopentyl-2-[4-(3-dimethylamino-prop-1-ynyl)-phenyl]-propionic acid (456 mg, 84%) as a brown foam: EI-HRMS m/e calcd for $C_{19}H_{25}NO_2$ ($M^+$) 299.1885, found 299.1885.

A solution of 3-cyclopentyl-2-[4-(3-dimethylamino-prop-1-ynyl)-phenyl]-propionic acid (150 mg, 0.50 mmol), benzotriazol-1-yloxytris(dimethylamino)phosphonium hexafluorophosphate (332 mg, 0.75 mmol), triethylamine (0.21 mL, 1.50 mmol) and 2-aminothiazole (86 mg, 0.86 mmol) in methylene chloride (5 mL) was stirred at 25° C. for 2 h. At this time, the reaction was diluted with methylene chloride (10 mL). This solution was washed with water (1×10 mL), a 1N aqueous sodium hydroxide solution (1×10 mL), and a half-saturated aqueous sodium chloride solution (1×10 mL). The aqueous layers were back extracted with methylene chloride (1×10 mL). The combined organic extracts were dried over sodium sulfate, filtered, and concentrated in vacuo. Flash chromatography (Merck Silica gel 60, 230–400 mesh, 95/5 methylene chloride/methanol) afforded 3-cyclopentyl-2-[4-(3-dimethylamino-prop-1-ynyl)-phenyl]-N-thiazol-2-yl-propionamide (37 mg, 19.3%) as a white solid: mp 164–167° C.; EI-HRMS m/e calcd for $C_{22}H_{27}N_3OS$ ($M^+$) 381.1874, found 381.1879.

EXAMPLE 8

3-Cyclopentyl-2-[4-(3-morpholin-4-yl-prop-1-ynyl)-phenyl]-N-thiazol-2-yl-propionamide

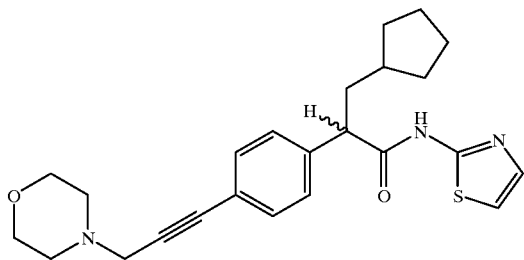

A solution of diisopropylamine (11.2 mL, 80.13 mmol) in tetrahydrofuran (120 mL) cooled to −78° C. was treated with a 2.5M solution of n-butyllithium in hexanes (32 mL, 80.13 mmol). This solution was stirred at −78° C. for 30 min and then treated with a solution of (4-iodo-phenyl)-acetic acid (9.67 g, 36.9 mmol) in tetrahydrofuran (88 mL) and 1,3-dimethyl-3,4,5,6-tetrahydro-2(1H)-pyrimidinone (29 mL). The reaction mixture was allowed to stir at −78° C. for 1 h. At this time, the reaction was treated with iodomethylcyclopentane (8.53 g, 40.6 mmol). The reaction mixture was allowed to slowly warm to 25° C. where it was stirred at 25° C. for 18 h. At this time, the reaction mixture was quenched with water (5 mL) and then concentrated in vacuo. The residue was diluted with water (800 mL) and then acidified to pH=2 with concentrated hydrochloric acid. This solution was extracted with ethyl acetate (2×800 mL). The combined organic extracts were washed with water (1×600 mL) and a saturated aqueous sodium chloride solution (1×600 mL), dried over sodium sulfate, filtered, and concentrated in vacuo. Flash chromatography (Merck Silica gel 60, 230–400 mesh, 50/50 hexanes/ethyl acetate) afforded 3-cyclopentyl-2-(4-iodo-phenyl)-propionic acid (7.34 g, 57.8%) as a white solid: mp 105–107° C.; EI-HRMS m/e calcd for $C_{14}H_{17}IO_2$ ($M^+$) 344.0273, found 344.0275.

A solution of 3-cyclopentyl-2-(4-iodo-phenyl)-propionic acid (7.18 g, 20.86 mmol) in methanol (150 mL) was treated with a catalytic amount of concentrated sulfuric acid (7 drops). The reaction mixture was heated at 70° C. for 18 h. At this time, the reaction was cooled to 25° C. and concentrated in vacuo. The residue was partitioned between ethyl acetate (400 mL) and a saturated aqueous sodium bicarbonate solution (400 mL). The aqueous layer was extracted with ethyl acetate (1×400 mL). The combined organic extracts were washed with a saturated aqueous sodium chloride solution (1×400 mL), dried over sodium sulfate, filtered, and concentrated in vacuo to afford 3-cyclopentyl-2-(4-iodo-phenyl)-propionic acid methyl ester (7.24 g, 96.9%) as an off-white solid: mp 51–54° C.; EI-HRMS m/e calcd for $C_{15}H_{19}IO_2$ ($M^+$) 358.0429, found 358.0419.

A solution of 3-cyclopentyl-2-(4-iodo-phenyl)-propionic acid methyl ester (716 mg, 2.0 mmol) and triethylamine (2 mL, 0.01 mmol) in N,N-dimethylformamide (2 mL) was treated with 4-prop-2-ynyl morpholine (626 mg, 5.0 mmol). The resulting reaction mixture was degassed with argon and then treated with cooper iodide (10 mg, 0.05 mmol) and bis(triphenylphosphine)palladium (II) chloride (15 mg, 0.02 mmol). The reaction was then heated at 70° C. for 24 h. At this time, the reaction was cooled to 25° C. and concentrated in vacuo. The residue was diluted with ethyl acetate (40 mL) and a half-saturated aqueous sodium chloride solution (1×20 mL). The aqueous layer was back extracted with ethyl acetate (1×40 mL). The combined organic extracts were washed with a half-saturated aqueous sodium chloride solution (1×20 mL), dried over sodium sulfate, filtered, and concentrated in vacuo. Flash chromatography (Merck Silica gel 60, 230–400 mesh, 60/40 ethyl acetate/hexanes) afforded 3-cyclopentyl-2-[4-(3-morpholin-4-yl-prop-1-ynyl)-phenyl]-propionic acid methyl ester (582 mg, 82%) as an amber oil: EI-HRMS m/e calcd for $C_{22}H_{29}NO_3$ ($M^+$) 355.2147, found 355.2150.

A solution of 3-cyclopentyl-2-[4-(3-morpholin-4-yl-prop-1-ynyl)-phenyl]-propionic acid methyl ester (575 mg, 1.62 mmol) in methanol (10 mL) and water (10 mL) was treated with lithium hydroxide (778 mg, 18.5 mmol). The reaction mixture was stirred at 25° C. for 5 h. At this time, the reaction was concentrated in vacuo. The residue was diluted with water (40 mL). This solution was acidified to pH=5 with concentrated hydrochloric acid and then extracted with ethyl acetate (2×40 mL). The combined organic extracts were then washed with a half-saturated aqueous sodium chloride solution (1×40 mL), dried over sodium sulfate, filtered, and concentrated in vacuo to afford 3-cyclopentyl-2-[4-(3-morpholin-4-yl-prop-1-ynyl)-phenyl]-propionic acid (601 mg, quant.) as a light brown oil: EI-HRMS m/e calcd for $C_{21}H_{27}NO_3$ ($M^+$) 341.1990, found 341.1996.

A solution of 3-cyclopentyl-2-[4-(3-morpholin-4-yl-prop-1-ynyl)-phenyl]-propionic acid (171 mg, 0.50 mmol), benzotriazol-1-yloxytris(dimethylamino)phosphonium hexafluorophosphate (332 mg, 0.75 mmol), triethylamine (0.21 mL, 1.50 mmol) and 2-aminothiazole (86 mg, 0.86 mmol) in methylene chloride (5 mL) was stirred at 25° C. for 2 h. At this time, the reaction was diluted with methylene chloride (10 mL). This solution was washed with water (1×10 mL), a 1N aqueous sodium hydroxide solution (1×10 mL), and a half-saturated aqueous sodium chloride solution (1×10 mL). The aqueous layers were back extracted with methylene chloride (1×10 mL). The combined organic extracts were dried over sodium sulfate, filtered, and concentrated in vacuo. Flash chromatography (Merck Silica gel 60, 230–400 mesh, 98/2 ethyl acetate/methanol) afforded 3-cyclopentyl-2-[4-(3-morpholin-4-yl-prop-1-ynyl)-phenyl]-N-thiazol-2-yl-propionamide (151 mg, 71.2%) as a white foam: EI-HRMS m/e calcd for $C_{24}H_{29}N_3O_2S$ ($M^+$) 423.1980, found 423.1980.

EXAMPLE 9

3-Cyclopentyl-2-(4-pyridin-2-ylethynyl-phenyl)-N-thiazol-2-yl-propionamide

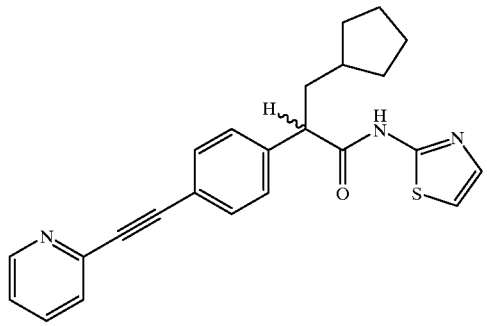

A solution of diisopropylamine (11.2 mL, 80.13 mmol) in tetrahydrofuran (120 mL) cooled to −78° C. was treated with a 2.5M solution of n-butyllithium in hexanes (32 mL, 80.13 mmol). This solution was stirred at −78° C. for 30 min and then treated with a solution of (4-iodo-phenyl)-acetic acid (9.67 g, 36.9 mmol) in tetrahydrofuran (88 mL) and 1,3-dimethyl-3,4,5,6-tetrahydro-2(1H)-pyrimidinone (29 mL). The reaction mixture was allowed to stir at −78° C. for 1 h. At this time, the reaction was treated with iodomethylcyclopentane (8.53 g, 40.6 mmol). The reaction mixture was allowed to slowly warm to 25° C. where it was stirred at 25° C. for 18 h. At this time, the reaction mixture was quenched with water (5 mL) and then concentrated in vacuo. The residue was diluted with water (800 mL) and then acidified to pH=2 with concentrated hydrochloric acid. This solution was extracted with ethyl acetate (2×800 mL). The combined organic extracts were washed with water (1×600 mL) and a saturated aqueous sodium chloride solution (1×600 mL), dried over sodium sulfate, filtered, and concentrated in vacuo. Flash chromatography (Merck Silica gel 60, 230–400 mesh, 50/50 hexanes/ethyl acetate) afforded 3-cyclopentyl-2-(4-iodo-phenyl)-propionic acid (7.34 g, 57.8%) as a white solid: mp 105–107° C.; EI-HRMS m/e calcd for $C_{14}H_{17}IO_2$ (M+) 344.0273, found 344.0275.

A solution of 3-cyclopentyl-2-(4-iodo-phenyl)-propionic acid (7.18 g, 20.86 mmol) in methanol (150 mL) was treated with a catalytic amount of concentrated sulfuric acid (7 drops). The reaction mixture was heated at 70° C. for 18 h. At this time, the reaction was cooled to 25° C. and concentrated in vacuo. The residue was partitioned between ethyl acetate (400 mL) and a saturated aqueous sodium bicarbonate solution (400 mL). The aqueous layer was extracted with ethyl acetate (1×400 mL). The combined organic extracts were washed with a saturated aqueous sodium chloride solution (1×400 mL), dried over sodium sulfate, filtered, and concentrated in vacuo to afford 3-cyclopentyl-2-(4-iodo-phenyl)-propionic acid methyl ester (7.24 g, 96.9%) as an off-white solid: mp 51–54° C.; EI-HRMS m/e calcd for $C_{15}H_{19}IO_2$ (M+) 358.0429, found 358.0419.

A solution of 3-cyclopentyl-2-(4-iodo-phenyl)-propionic acid methyl ester (1.0 g, 2.79 mmol) and triethylamine (4 mL, 0.02 mmol) in N,N-dimethylformamide (4 mL) was treated with 2-ethynylpyridine (345 mg, 3.34 mmol). The resulting reaction mixture was degassed with argon for 10 min and then treated with cooper iodide (168 mg, 0.88 mmol) and bis(triphenylphosphine)palladium (II) chloride (305 mg, 0.44 mmol). The reaction was then heated at 70° C. for 1.5 h. At this time, the reaction was cooled to 25° C. and concentrated in vacuo. Flash chromatography (Merck Silica gel 60, 230–400 mesh, 80/20 hexanes/ethyl acetate) afforded 3-cyclopentyl-2-(4-pyridin-2-ylethynyl-phenyl)-propionic acid methyl ester (900 mg, 97%) as a yellow oil: EI-HRMS m/e calcd for $C_{22}H_{23}NO_2$ (M+) 333.1728, found 333.1724.

A solution of 3-cyclopentyl-2-(4-pyridin-2-ylethynyl-phenyl)-propionic acid methyl ester (930 mg, 2.79 mmol) in methanol (5 mL), water (2 mL) and tetrahydrofuran (1 mL) was treated with lithium hydroxide (80 mg, 1.90 mmol). The reaction mixture was stirred at 25° C. for 60 h. At this time, additional lithium hydroxide (100 mg, 2.38 mmol) was added. The reaction was stirred at 25° C. for 3 h. At this time, the reaction was diluted with water (10 mL) and then concentrated in vacuo. The resulting aqueous layer was washed with ethyl acetate (2×10 mL), acidified with a 1N aqueous hydrochloric acid solution, and then extracted with ethyl acetate (2×25 mL). The combined organic extracts were dried over magnesium sulfate, filtered and concentrated in vacuo to afford 3-cyclopentyl-2-(4-pyridin-2-ylethynyl-phenyl)-propionic acid (873 mg, 98%) as an amber solid: mp 143–147° C.; EI-HRMS m/e calcd for $C_{21}H_{21}NO_2$ (M+) 319.1572, found 319.1580.

A solution of 3-cyclopentyl-2-(4-pyridin-2-ylethynyl-phenyl)-propionic acid (150 mg, 0.47 mmol), benzotriazol-1-yloxytris(dimethylamino)phosphonium hexafluorophosphate (332 mg, 0.75 mmol), triethylamine (0.20 mL, 1.41 mmol) and 2-aminothiazole (75 mg, 0.75 mmol) in methylene chloride (5 mL) was stirred at 25° C. for 18 h. At this time, the reaction was diluted with water (10 mL). The organic phase was separated and washed with a 1N aqueous sodium hydroxide solution, and a saturated aqueous sodium chloride solution. The aqueous layers were each back-extracted with methylene chloride. The combined organic extracts were dried over magnesium sulfate, filtered, and concentrated in vacuo. Flash chromatography (Merck Silica gel 60, 230–400 mesh, 60/40 hexanes/ethyl acetate) afforded 3-cyclopentyl-2-(4-pyridin-2-ylethynyl-phenyl)-N-thiazol-2-yl-propionamide (134 mg, 71%) as a pale yellow solid: mp 185–187° C.; EI-HRMS m/e calcd for $C_{24}H_{23}N_3OS$ (M+) 401.1561, found 401.1555.

EXAMPLE 10

3-Cyclopentyl-2-(4-pyrimidin-5-ylethynyl-phenyl)-N-thiazol-2-yl-propionamide

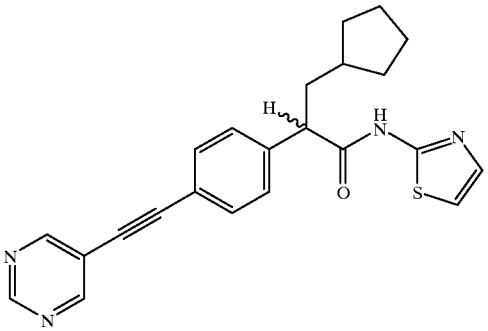

A solution of diisopropylamine (11.2 mL, 80.13 mmol) in tetrahydrofuran (120 mL) cooled to −78° C. was treated with a 2.5M solution of n-butyllithium in hexanes (32 mL, 80.13 mmol). This solution was stirred at −78° C. for 30 min and then treated with a solution of (4-iodo-phenyl)-acetic acid (9.67 g, 36.9 mmol) in tetrahydrofuran (88 mL) and 1,3-dimethyl-3,4,5,6-tetrahydro-2(1H)-pyrimidinone (29 mL). The reaction mixture was allowed to stir at −78° C. for 1 h. At this time, the reaction was treated with iodomethylcyclopentane (8.53 g, 40.6 mmol). The reaction mixture was allowed to slowly warm to 25° C. where it was stirred at 25° C. for 18 h. At this time, the reaction mixture was quenched with water (5 mL) and then concentrated in vacuo. The residue was diluted with water (800 mL) and then acidified to pH=2 with concentrated hydrochloric acid. This solution was extracted with ethyl acetate (2×800 mL). The combined organic extracts were washed with water (1×600 mL), a saturated aqueous sodium chloride solution (1×600 mL), dried over sodium sulfate, filtered, and concentrated in vacuo. Flash chromatography (Merck Silica gel 60, 230–400 mesh, 50/50 hexanes/ethyl acetate) afforded 3-cyclopentyl-2-(4-iodo-phenyl)-propionic acid (7.34 g, 57.8%) as a white solid: mp 105–107° C.; EI-HRMS m/e calcd for $C_{14}H_{17}IO_2$ (M+) 344.0273, found 344.0275.

A solution of 3-cyclopentyl-2-(4-iodo-phenyl)-propionic acid (7.18 g, 20.86 mmol) in methanol (150 mL) was treated with a catalytic amount of concentrated sulfuric acid (7 drops). The reaction mixture was heated at 70° C. for 18 h. At this time, the reaction was cooled to 25° C. and concentrated in vacuo. The residue was partitioned between ethyl acetate (400 mL) and a saturated aqueous sodium bicarbonate solution (400 mL). The aqueous layer was extracted with ethyl acetate (1×400 mL). The combined organic extracts were washed with a saturated aqueous sodium chloride solution (1×400 mL), dried over sodium sulfate, filtered, and concentrated in vacuo to afford 3-cyclopentyl-2-(4-iodo-phenyl)-propionic acid methyl ester (7.24 g, 96.9%) as an off-white solid: mp 51–54° C.; EI-HRMS m/e calcd for $C_{15}H_{19}IO_2$ (M+) 358.0429, found 358.0419.

A solution of 3-cyclopentyl-2-(4-iodo-phenyl)-propionic acid methyl ester (719 mg, 2.01 mmol) and triethylamine (3 mL, 0.015 mmol) in N,N-dimethylformamide (3 mL) was treated with 5-ethynyl-pyrimidine (230 mg, 2.21 mmol). The resulting reaction mixture was degassed with argon for 10 min and then treated with cooper iodide (92 mg, 0.48 mmol) and bis(triphenylphosphine)palladium (II) chloride (169 mg, 0.24 mmol). The reaction was stirred at 25° C. for 18 h and then heated at 67° C. for 2 h. At this time, the reaction was cooled to 25° C. and concentrated in vacuo. Flash chromatography (Merck Silica gel 60, 230–400 mesh, 80/20 hexanes/ethyl acetate) afforded 3-cyclopentyl-2-(4-pyrimidin-5-ylethynyl-phenyl)-propionic acid methyl ester (440 mg, 66%) as an orange oil: EI-HRMS m/e calcd for $C_{21}H_{22}N_2O_2$ (M+) 334.1681, found 334.1681.

A solution of 3-cyclopentyl-2-(4-pyrimidin-5-ylethynyl-phenyl)-propionic acid methyl ester (440 mg, 1.32 mmol) in methanol (3 mL), water (2 mL), and tetrahydrofuran (0.5 mL) was treated with lithium hydroxide (38 mg, 0.90 mmol). The reaction mixture was stirred at 25° C. for 60 h. At this time, additional lithium hydroxide (38 mg, 0.90 mmol) was added. The reaction was stirred at 25° C. for 4 h. At this time, the reaction was diluted with water (5 mL) and then concentrated in vacuo. The resulting aqueous layers were washed with ethyl acetate (2×10 mL), acidified with a 1N aqueous hydrochloric acid solution, and then extracted with ethyl acetate (2×25 mL). The combined organic extracts were dried over magnesium sulfate, filtered, and concentrated in vacuo to afford 3-cyclopentyl-2-(4-pyrimidin-5-ylethynyl-phenyl)-propionic acid (390 mg, 92%) as an amber foam: EI-HRMS m/e calcd for $C_{20}H_{20}N_2O_2$ (M+) 320.1524, found 320.1526.

A solution of 3-cyclopentyl-2-(4-pyrimidin-5-ylethynyl-phenyl)-propionic acid (150 mg, 0.53 mmol), benzotriazol-1-yloxytris(dimethylamino)phosphonium hexafluorophosphate (376 mg, 0.85 mmol), triethylamine (0.22 mL, 1.59 mmol) and 2-aminothiazole (85 mg, 0.85 mmol) in methylene chloride (5 mL) was stirred at 25° C. for 18 h. At this time, the reaction was diluted with water (10 mL). The organic phase was separated and washed with a 1N aqueous sodium hydroxide solution, and a saturated aqueous sodium chloride solution. The aqueous layers were each back-extracted with methylene chloride. The combined organic extracts were dried over magnesium sulfate, filtered, and concentrated in vacuo. Flash chromatography (Merck Silica gel 60, 230–400 mesh, 60/40 hexanes/ethyl acetate) afforded 3-cyclopentyl-2-(4-pyrimidin-5 -ylethynyl-phenyl)-N-thiazol-2-yl-propionamide (102 mg, 54%) as a white solid: mp 149–151 ° C.; EI-HRMS m/e calcd for $C_{23}H_{22}N_4OS$ (M+) 402.1514, found 402.1516.

Biological Activity Examples

EXAMPLE A

In Vitro Glucokinase Activity

Glucokinase Assay: Glucokinase (GK) was assayed by coupling the production of glucose-6-phosphate to the generation of NADH with glucose-6-phosphate dehydrogenase (G6PDH, 0.75–1 kunits/mg; Boehringer Mannheim, Indianapolis, Ind.) from *Leuconostoc mesenteroides* as the coupling enzyme (Scheme 2). Recombinant Scheme 2

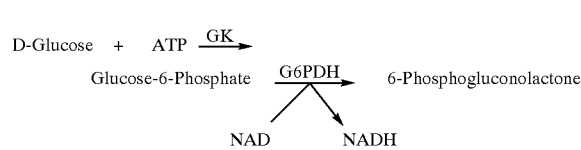

Human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 μl. The incubation mixture contained: 25 mM Hepes buffer (pH, 7.1), 25 mM KCl, 5 mM D-glucose, 1 mM ATP, 1.8 mM NAD, 2 mM $MgCl_2$, 1 μM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes that were from Sigma Chemical Co, St Louis, Mo. Test compounds were dissolved in DMSO and were added to the incubation mixture minus GST-GK in a volume of 12 μl to yield a final DMSO concentration of 10%. This mix was preincubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μl GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO, but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the $SC_{1.5}$, was calculated. All of the compounds of formula I described in the Synthesis Examples had an $SC_{1.5}$ less than or equal to 30 μM.

EXAMPLE C

Tablets containing the following ingredients can be produced in a conventional manner:

| Ingredients | mg per tablet |
|---|---|
| Compound of formula (I) | 10.0–100.0 |
| Lactose | 125.0 |
| Corn starch | 75.0 |
| Talc | 4.0 |
| Magnesium stearate | 1.0 |

EXAMPLE D

Capsules containing the following ingredients can be produced in a conventional manner:

| Ingredients | mg per tablet |
|---|---|
| Compound of formula (I) | 25.0 |
| Lactose | 150.0 |
| Corn starch | 20.0 |
| Talc | 5.0 |

What is claimed is:
1. A compound of the formula:

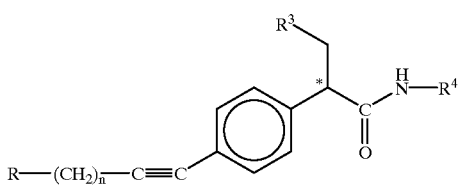

I wherein R is hydrogen, lower alkyl, hydroxy lower alkyl, lower alkoxy lower alkyl,

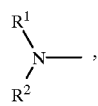

an unsubstituted or hydroxy substituted cycloalkyl ring containing 5 or 6 carbon atoms, a five- or six-membered saturated heterocyclic ring which contains from 1 to 3 hetero ring atoms selected from the group consisting of sulfur, oxygen or nitrogen, or an unsubstituted five- or six-membered heteroaromatic ring, connected by a ring carbon atom, which contains from 1 to 3 heteroatoms in the ring selected from the group consisting of sulfur, nitrogen and oxygen; $R^3$ is cycloalkyl having 3 to 7 carbon atoms; $R^4$ is an unsubstituted or mono-substituted five- or six-membered heteroaromatic ring, connected by a ring carbon atom to the amine group shown, which five- or six-membered heteroaromatic ring contains from 1 to 3 heteroatoms selected from sulfur, oxygen or nitrogen, with one heteroatom being nitrogen adjacent to the connecting ring carbon atom; said mono-substituted heteroaromatic ring being monosubstituted at a position on a ring carbon atom other than adjacent to said connecting carbon atom with a substituent selected from the group consisting of lower alkyl, halo, nitro, cyano, —(CH$_2$)$_m$—OR$^6$,

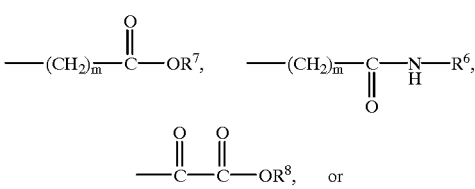

—(CH$_2$)$_m$—NHR$^6$;

n is the integer 0, 1 or 2;

m is 0, 1, 2, 3 or 4;

$R^1$, $R^2$, $R^6$, $R^7$ and $R^8$ are independently hydrogen or lower alkyl and * designates the assymetric carbon atom center;

or a pharmaceutically acceptable salt thereof.

2. The compound of claim 1 wherein $R^3$ is cyclopentyl.

3. The compound of claim 2 wherein $R^4$ is an unsubstituted or monosubstituted five membered heteroaromatic ring.

4. The compound of claim 3 wherein $R^4$ is unsubstituted or monosubstituted thiazolyl.

5. The compound of claim 4 wherein R is hydrogen or lower alkyl.

6. The compound of claim 5 wherein said compound is 3-cyclopentyl-2-(4-ethynyl-phenyl)-N-thiazol-2-yl-propionamide.

7. The compound of claim 4 wherein R is hydroxy lower alkyl or lower alkoxy lower alkyl.

8. The compound of claim 7 wherein $R^4$ is unsubstituted thiazolyl.

9. The compound of claim 8 wherein said compound is 3-cyclopentyl-2-[4-(3-methoxy-prop-1-ynyl)-phenyl]-N-thiazol-2-yl-propionamide.

10. The compound of claim 8 wherein said compound is 3-cyclopentyl-2-[4-(3-hydroxy-3-methyl-pent-1-ynyl)-phenyl]-N-thiazol-2-yl-propionamide.

11. The compound of claim 8 wherein said compound is 3-cyclopentyl-2-[4-(4-hydroxy-pent-1-ynyl)-phenyl]-N-thiazol-2-yl-propionamide.

12. The compound of claim 8 wherein said compound is 3-cyclopentyl-2-[4-(3-hydroxy-prop-1-ynyl)-phenyl]-N-thiazol-2-yl-propionamide.

13. The compound of claim 7 wherein $R^4$ is thiazolyl monosubstituted with

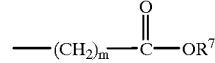

and m and $R^7$ are as above.

14. The compound of claim 13 wherein said compound is 2-{3-cyclopentyl-2-[4-(3-methoxy-prop-1-ynyl)-phenyl]-propionylamino}-thiazole-4-carboxylic acid ethyl ester.

15. The compound of claim 4 wherein R is

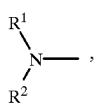

and $R^1$ and $R^2$ are as above.

16. The compound of claim 15 wherein $R^4$ is unsubstituted thiazolyl.

17. The compound of claim 16 wherein said compound is 3-cyclopentyl-2-[4-(3-dimethylamino-prop-1-ynyl)-phenyl]-N-thiazol-2-yl-propionamide.

18. The compound of claim 3 wherein $R^4$ is an unsubstituted thiazolyl.

19. The compound of claim 18 wherein R is an unsubstituted or hydroxy substituted cycloalkyl ring containing from 5 to 6 carbon atoms.

20. The compound of claim 19 wherein said compound is 3-cyclopentyl-2-[4-(1-hydroxy-cyclohexylethynyl)-phenyl]-N-thiazol-2-yl-propionamide.

21. The compound of claim 18 wherein said compound is R is a five- or six-membered saturated heterocyclic ring containing from 1 to 2 heteroatoms selected from the group consisting of oxygen or nitrogen.

22. The compound of claim 21 wherein said compound is 3-cyclopentyl-2-[4-(3-morpholin-4-yl-prop-1-ynyl)-phenyl]-N-thiazol-2-yl-propionamide.

23. The compound of claim 18 wherein R is an unsubstituted five- or six-membered heteroaromatic ring containing from 1 to 2 heteroatoms in the ring selected from the group consisting of sulfur, nitrogen and oxygen.

24. The compound of claim 23 wherein said compound is 3-cyclopentyl-2-(4-pyridin-2-ylethynyl-phenyl)-N-thiazol-2-yl-propionamide.

25. The compound of claim 23 wherein said compound is 3-cyclopentyl-2-(4-pyrimidin-5-ylethynyl-phenyl)-N-thiazol-2-yl-propionamide.

* * * * *